United States Patent [19]

Steuer et al.

[11] 4,407,295

[45] Oct. 4, 1983

[54] MINIATURE PHYSIOLOGICAL MONITOR WITH INTERCHANGEABLE SENSORS

[75] Inventors: Robert R. Steuer; Robert K. Rogers, both of Salt Lake City; Robert H. Horne, Holladay, all of Utah

[73] Assignee: DNA Medical, Inc., Salt Lake City, Utah

[21] Appl. No.: 197,704

[22] Filed: Oct. 16, 1980

[51] Int. Cl.³ .............................................. A61B 5/02
[52] U.S. Cl. ................................... 128/670; 128/671; 128/736; 128/725
[58] Field of Search ................. 128/666, 672, 687–690

[56] References Cited

U.S. PATENT DOCUMENTS

| | | | |
|---|---|---|---|
| 3,107,664 | 10/1963 | Smith | 128/2.05 |
| 3,202,149 | 8/1965 | Emmons | 128/2.05 |
| 3,230,951 | 1/1966 | Teschner | 128/2.05 |
| 3,581,570 | 6/1971 | Wortz | 128/736 |
| 3,704,706 | 12/1972 | Herczfeld et al. | 128/2 R |
| 3,717,140 | 2/1973 | Greenwood | 128/2.05 T |
| 3,858,574 | 1/1975 | Page | 128/666 |
| 3,908,636 | 9/1975 | Page | 128/2.05 T |
| 3,908,640 | 9/1975 | Page | 128/2.05 T |
| 4,009,708 | 3/1977 | Fay, Jr. | 128/2.05 P |
| 4,015,595 | 4/1977 | Benjamin, Jr. | 128/2.05 V |
| 4,030,483 | 6/1977 | Stevens | 128/2.05 T |
| 4,058,118 | 11/1977 | Stupay et al. | 128/2.05 P |
| 4,086,916 | 5/1978 | Freeman et al. | 128/2.05 T |
| 4,090,504 | 5/1978 | Nathan | 128/2.05 R |
| 4,120,294 | 10/1978 | Wolfe | 128/2.05 T |
| 4,120,296 | 10/1978 | Prinz | 128/2.05 T |
| 4,185,621 | 1/1980 | Morrow | 128/690 X |
| 4,195,642 | 4/1980 | Price et al. | 128/689 |
| 4,198,988 | 4/1980 | Cash, Jr. et al. | 128/666 |
| 4,202,350 | 5/1980 | Walton | 128/690 |
| 4,224,948 | 9/1980 | Cramer et al. | 128/690 |
| 4,230,127 | 10/1980 | Larson | 128/706 |
| 4,280,506 | 7/1981 | Zurcher | 128/690 |
| 4,301,808 | 11/1981 | Tans | 128/689 |
| 4,305,401 | 12/1981 | Reissmueller et al. | 128/690 |
| 4,906,854 | 6/1978 | Perica et al. | 128/2.05 T |

Primary Examiner—Kyle L. Howell
Assistant Examiner—Francis J. Jaworski
Attorney, Agent, or Firm—Fleit, Jacobson & Cohn

[57] ABSTRACT

A miniature portable physiological parameter measuring system with interchangeable sensors. In a preferred embodiment, the system is incorporated into a wrist-worn device having the general configuration of a wristwatch. The device contains, in the upper right-hand quadrant, an outcropping on which a pulse sensor is located. In the lower left-hand quadrant of the device, when worn of the left hand, diagonally opposite from the sensor described above, there is positioned a tiny plug. When the plug is removed, an open area is displayed which allows for the introduction of a connector in the wrist device. On introduction of the connector into the side of the device, the permanent sensor housed within the wrist device is disconnected and the remote sensor commences inputting a signal into the wrist device. The remote sensor enables a pulse to be taken off the finger of the same hand where the wrist device is located, or any other finger, as well as to take the pulse using a different type of remote sensor such as one for the use on the earlobe. Through the use of other sensors for measuring such parameters as lung capacity, temperature, and respiration, to name a few, the wrist device can be used as a dedicated display of whatever input it receives from the remote sensor. Specific examples of remote sensors for measuring physiological parameters on the earlobe and the finger are also provided.

8 Claims, 18 Drawing Figures

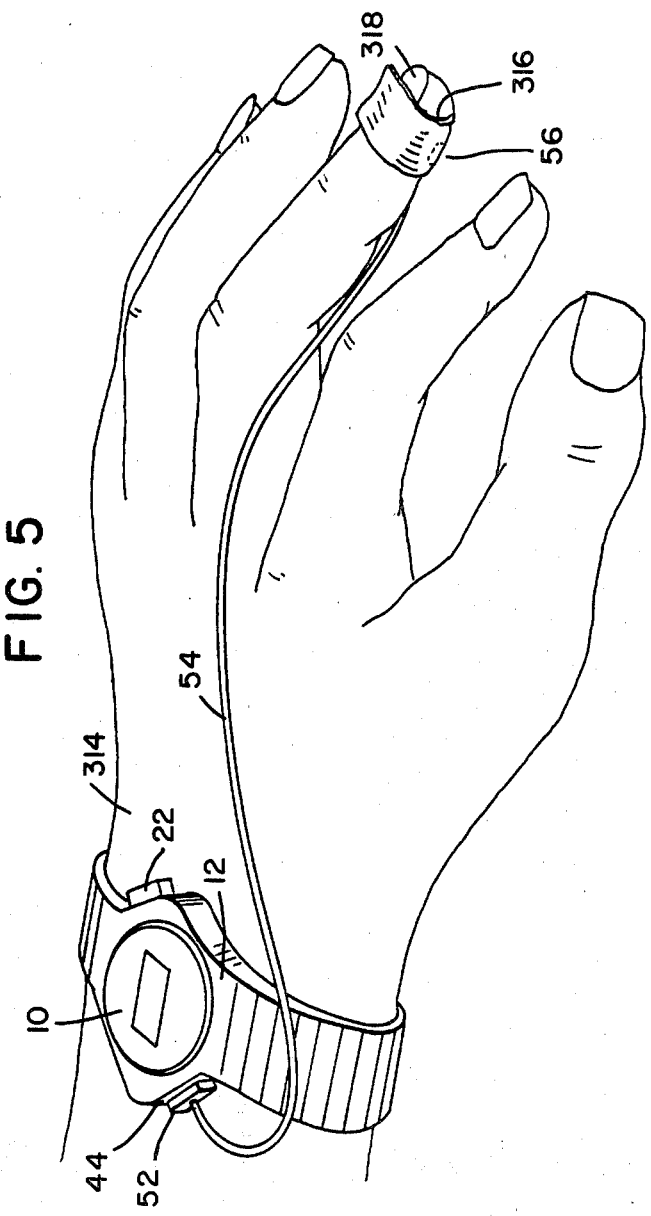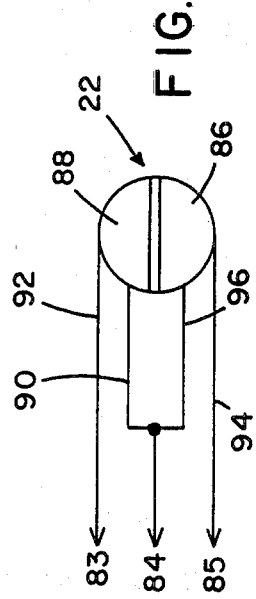

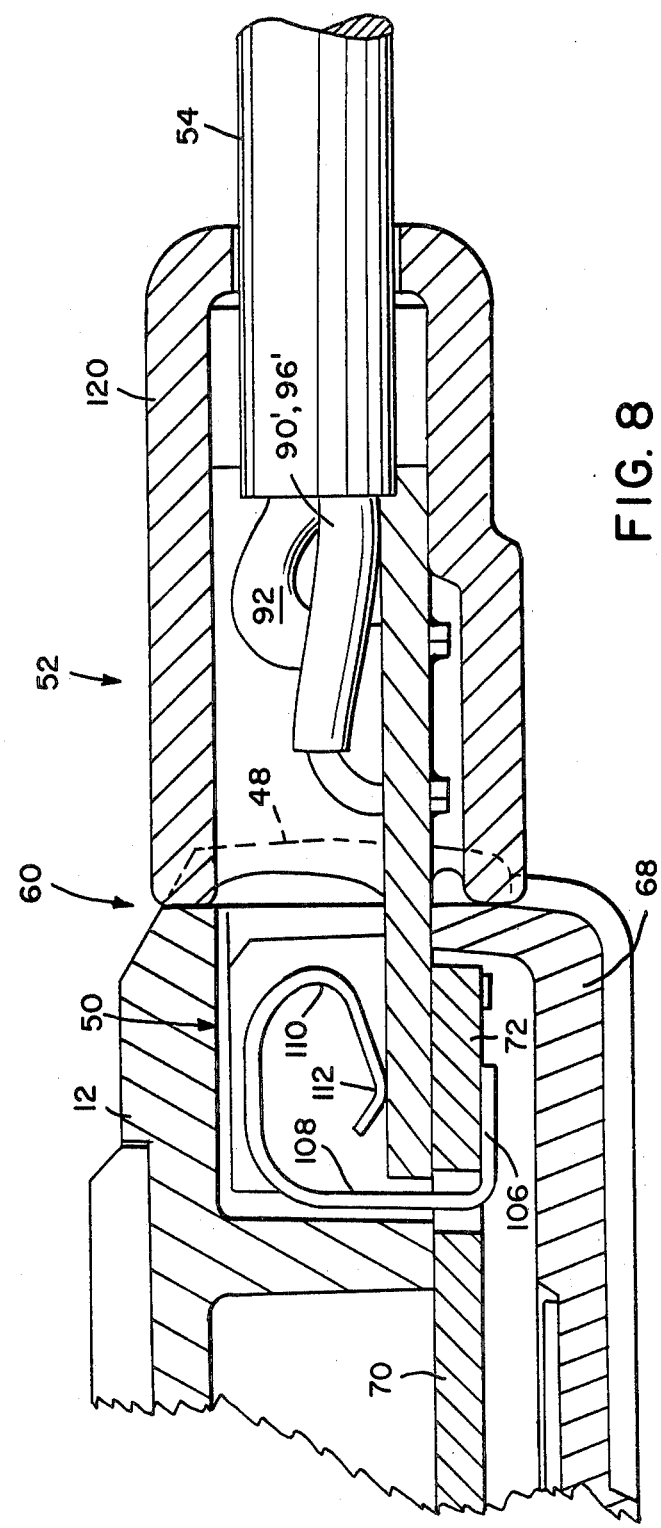

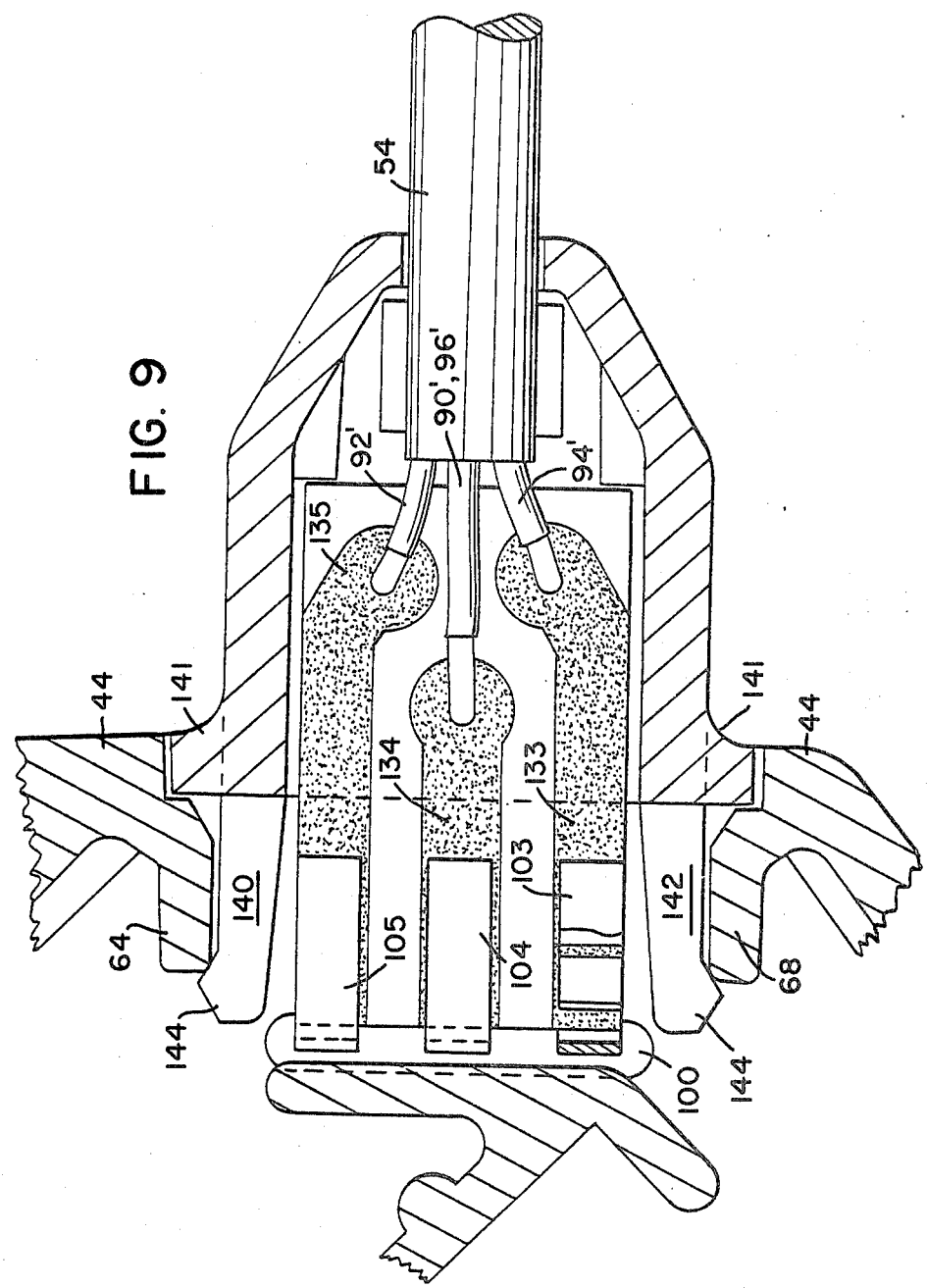

MINIATURE PHYSIOLOGICAL MONITOR WITH INTERCHANGEABLE SENSORS

BACKGROUND OF THE INVENTION

1. Field of the Invention

The present invention relates to miniature physiological monitors with visual readout, in general, and to a miniature physiological monitor using interconnectable sensors to display various functions and indicies of the human body whether they be dynamic or static measurements.

2. Description of the Prior Art

A number of miniature devices are known for measuring a specific physiological parameter such as pulse rate. Some of these devices are embodied in wristwatches and employ various methods for sensing the pulse of a user. However, these devices have limited use because of their inability to accurately and repeatedly produce true readings.

On the other hand, there are numerous electronic patient monitoring systems for hospital use which produce highly accurate readings at greatly increased cost. Typically, such systems include a number of stations, one associated with each patient, connected with a central monitoring console. Typically, the electronic patient systems simultaneously monitor several different body functions or parameters and the patient must be fitted with numerous sensors both of the invasive and non-invasive type. Because the monitoring systems are quite expensive to purchase and operate, it is inefficient to use them when it is only necessary to monitor but a few physiological parameters.

There is thus a need for a miniature, portable physiological parameter measuring system which displays highly accurate readings and which is made versatile through the use of a number of interchangeable sensors so that a user may selectively monitor only those parameters of interest. The present invention is directed toward filling that need.

SUMMARY OF THE INVENTION

The present invention relates to a miniature portable physiological parameter measuring system with interchangeable sensors. In a preferred embodiment, the system is incorporated into a wrist-worn device having the general configuration of a wristwatch. The side of the device contains an outcropping within which a pulse sensor is located. When the device is worn on the left wrist, the user preferably places the pad of his right index finger, or any other finger, over the sensor area and the wrist device will commence picking up the pulse signal in the form of systolic beats the subsequent display. The wrist device also includes an audio beeper, a time-of-day feature, a chronograph stop-watch. Provision is made for other features such as automatic shut-off and fail-safe warning for battery depletion.

The location of the sensor, in the upper right-hand quadrant when the device is worn on the left wrist, enables the user to place his right hand on top of his left hand and place the index finger of the right hand over the sensor. This reduces movement artifact and muscle artifact normally accompanying other locations of the sensor.

In the lower left-hand quadrant of the device, when worn on the left hand, diagonally opposite from the sensor described above, there is positioned a tiny plug or cover. When the plug is removed, an open area is displayed which allows for the introduction of a connector into the wrist device. On introduction of the connector into the side of the device, the permanent sensor housed within the wrist device is disconnected and a remote sensor, attached to the connector, commences inputting a pulse information signal into the wrist device. The remote sensor enables a pulse to be taken off the finger of the same hand where the wrist device is located, or any other finger, as well as to take the pulse using a different type of remote sensor such as one for use on the earlobe.

Through the use of other remote sensors for measuring such parameters as lung capacity, temperature, and respiration, to name a few, the wrist device can be used as a dedicated display of whatever input it receives from the remote sensor.

It is contemplated that the wrist device could be replaced by a hand held device which could be placed in a briefcase or purse. The teachings of the subject invention could also be incorporated into a stethoscope, a pen, a ring, an earring, or in other possible wearable or portable configurations.

Thus, it is an object of the present invention to provide a wearable physiological monitor using a host of interconnectable sensors to display various functions and indicies of the human body whether they be dynamic or static measurements.

It is another object of the present invention to provide a master unit for taking an incoming information signal from a family of remote sensors and converting the signals into an eye-readable form for display.

It is a further object of the present invention to provide a universal display unit for displaying information sensed by a host of remote physiological parameter measuring sensors.

It is still an object of the present invention to provide a family of remote physiological parameter measuring sensors, where each sensor contains appropriate circuitry for converting a measured parameter into a suitable input signal for display by a master unit.

It is yet an object of the present invention to provide a connector assembly for electrically connecting a remote physiological parameter sensor to a dedicated display device.

It is still a further object of the present invention to provide an improved physiological parameter sensor for use on the finger.

It is yet a further object of the present invention to provide an improved physiological parameter sensor for use on the earlobe.

Additional objects of the present invention will become apparent from a reading of the specification and appended claims in which preferred, but not necessarily the only forms of the invention will be described in detail, taken in connection with the drawings accompanying and forming part of the application.

BRIEF DESCRIPTION OF THE DRAWINGS

FIG. 5 is a perspective view used to explain an additional way in which the device of FIG. 1 is used.

FIG. 7c is a schematic diagram used to explain the electrical connection of the sensor of FIG. 3 to the female connector.

FIG. 8 is a longitudinal section of the connector assembly joined together.

FIG. 9 is a top plan view of the connector assembly of FIG. 8 with top surfaces of the wrist device (partially shown) and the male connector removed.

FIG. 11b is an exploded perspective viewed from the left showing the remote ear sensor of FIG. 11a.

DETAILED DESCRIPTION OF THE DRAWINGS

Figure 1:
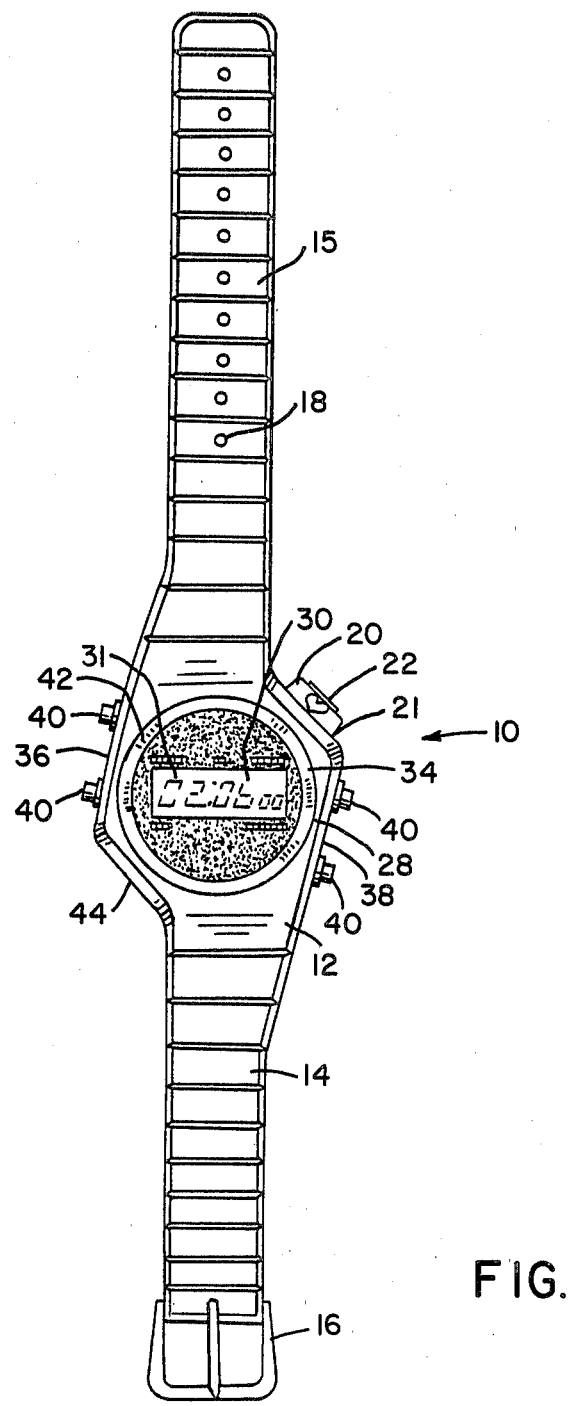
FIG. 1 is a top plan view of a wrist-worn device embodying the teachings of the present invention.

With reference to FIGS. 1-5, the subject invention is shown in the context of a device wearable upon the wrist of a user. As will become evident hereinafter, it is also possible that the teachings of the subject invention could be embodied in a hand held device that could be placed in a briefcase or purse, in a stethoscope, in a pendant, in a pen clipped to the clothing, in a ring, earring, or in any other possible wearable or portable configuration. It is also possible to employ many of the teachings of the present invention in a non-portable unit for home and professional use. However, for purposes of a preferred embodiment, the device will be described in the context of a device wearable upon the wrist.

The wrist-worn device, generally designated as 10, has a configuration which is similar to a digital wristwatch. The device 10 includes a two-piece housing or main body portion 12 to which is secured, by conventional means, a pair of wrist straps 14 and 15. Wrist strap 14 terminates at its free end in a clasp 16, whereas wrist strap 15 contains a number of apertures 18 longitudinally disposed along the length of the strap. Thus, it can be seen that the device is mounted on the wrist in a manner similar to that of a conventional wristwatch.

With reference to its orientation in FIG. 1, the main body 12, in its upper right-hand quadrant, defines a side surface 21 that contains a tiny outcropping 20. Positioned within the outcropping is a sensor 22 whose face 17 protrudes slightly out of the outcropping. When the device is worn on the left hand, the user preferably places his right index finger, or any other finger, over the sensor 22 and the device will pick up a pulse signal, in a manner to be described in greater detail hereinafter.

The main body 12 defines a top or outer surface 24 and a back or inner surface 26. Normally, the back surface presses up against the skin of the user when the device is being worn. In this way, the outer surface, which contains a display 30, is in plain sight of the user. Thus, there is defined by the outer surface an aperture 28 within which is mounted a digital display device 30. The display is protected by a conventional crystal cover 32 which is secured to the main body portion by a securing rim 34 in known manner. The display 30 comprises a preselected number of numeric display elements 31 arranged one next to the other. These elements define a universal display format for the physiological parameters measured by the device.

The main body 12 also defines opposed side walls 36 and 38, each of which receives a pair of push-buttons 40. The rim 34 contains indicia 42 appropriately placed opposite the various push-buttons 40 as well as the outcropping 20 to provide certain instructions and reminders to the user regarding the operation of the device.

Figure 2:
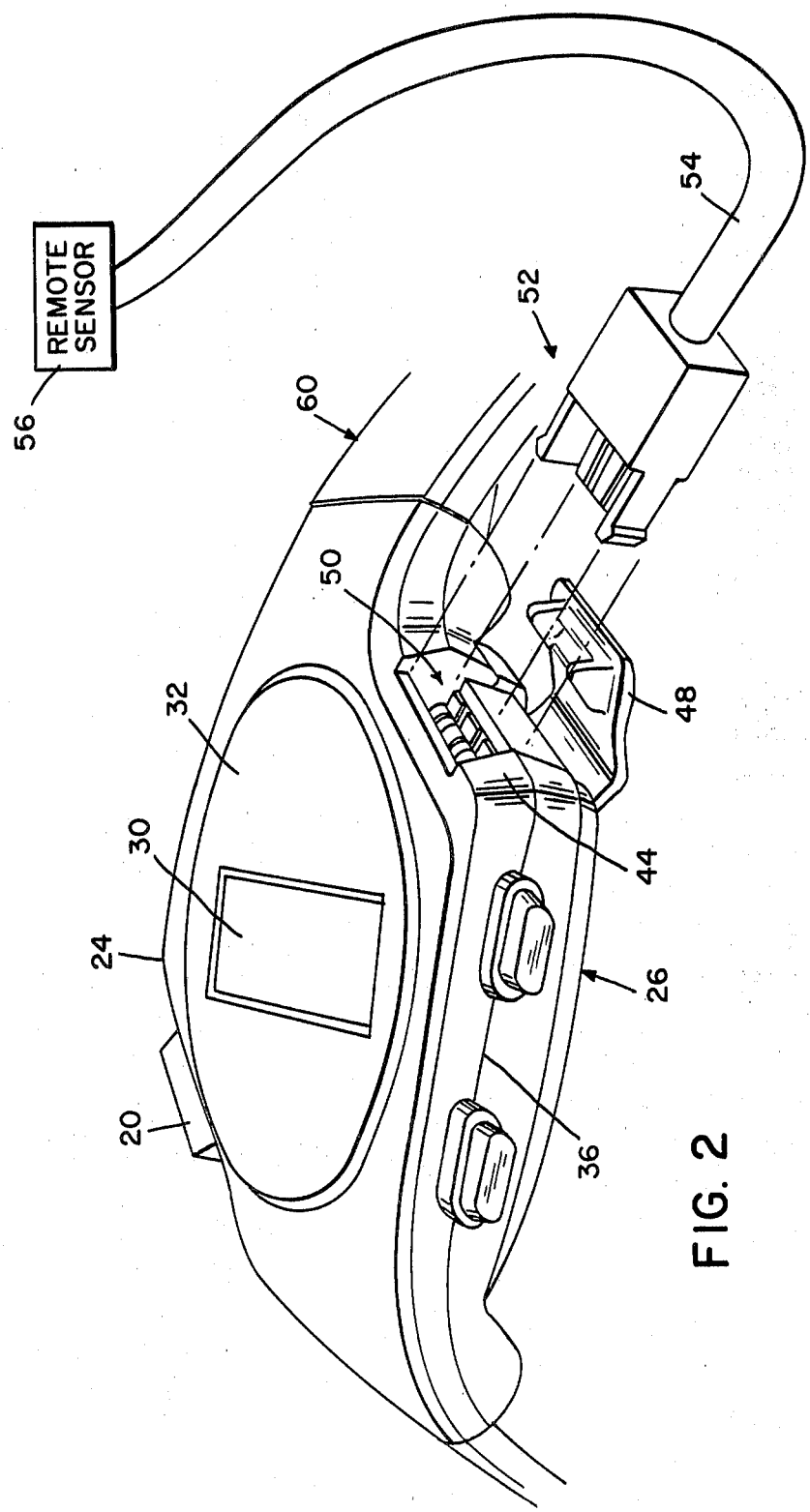
FIG. 2 is a perspective view of the device of FIG. 1 showing a connector assembly for using a remote physiological parameter sensor.

The main body 12 contains an additional side wall 44 bounded by the edge of side wall 36 and one edge of the strap 14. In addition, the surface of side wall 44 is diagonally opposite from the surface of side wall 21. Affixed to the main body by conventional means is a resilient flap or plug 48 which when opened, as shown in FIG. 2, reveals a female connector generally designated as 50. It is to be understood that the flap 48 may be secured to the main body 12 by any well-known means, such as thermal bonding, and could be formed as part of the main body should the body be produced by injection moulding of plastic.

The female connector, which will be discribed in greater detail hereinafter, is configured to receive a male connector generally designated as 52, which is electrically connected to wire leads 54. The male and female connectors together form connector assembly 60. The other end of the wire leads 54 are electrically connected to a remote physiological parameter sensor 56. In terms of the embodiment shown in FIG. 2, sensor 56 is typically a light-emitting diode/photocell combination which measures the systolic beats of the user. The same applies to sensor 22.

Mounted within the housing (a portion of which is shown in FIG. 7) is a printed circuit board 70 which contains appropriate circuitry for converting physiological information sensed by either sensor 22 or sensor 56, into an eye-readable format on digital display 30. An example of appropriate circuitry is disclosed in copending U.S. patent application Ser. No. 9823, entitled "Cardiotachometer Using Auto Correlation Techniques," filed Feb. 6, 1979, now U.S. Pat. No. 4,239,048 and is incorporated by reference herein. The details of this circuitry, as it relates to the present invention, will be described in greater detail hereinafter.

Figure 4:
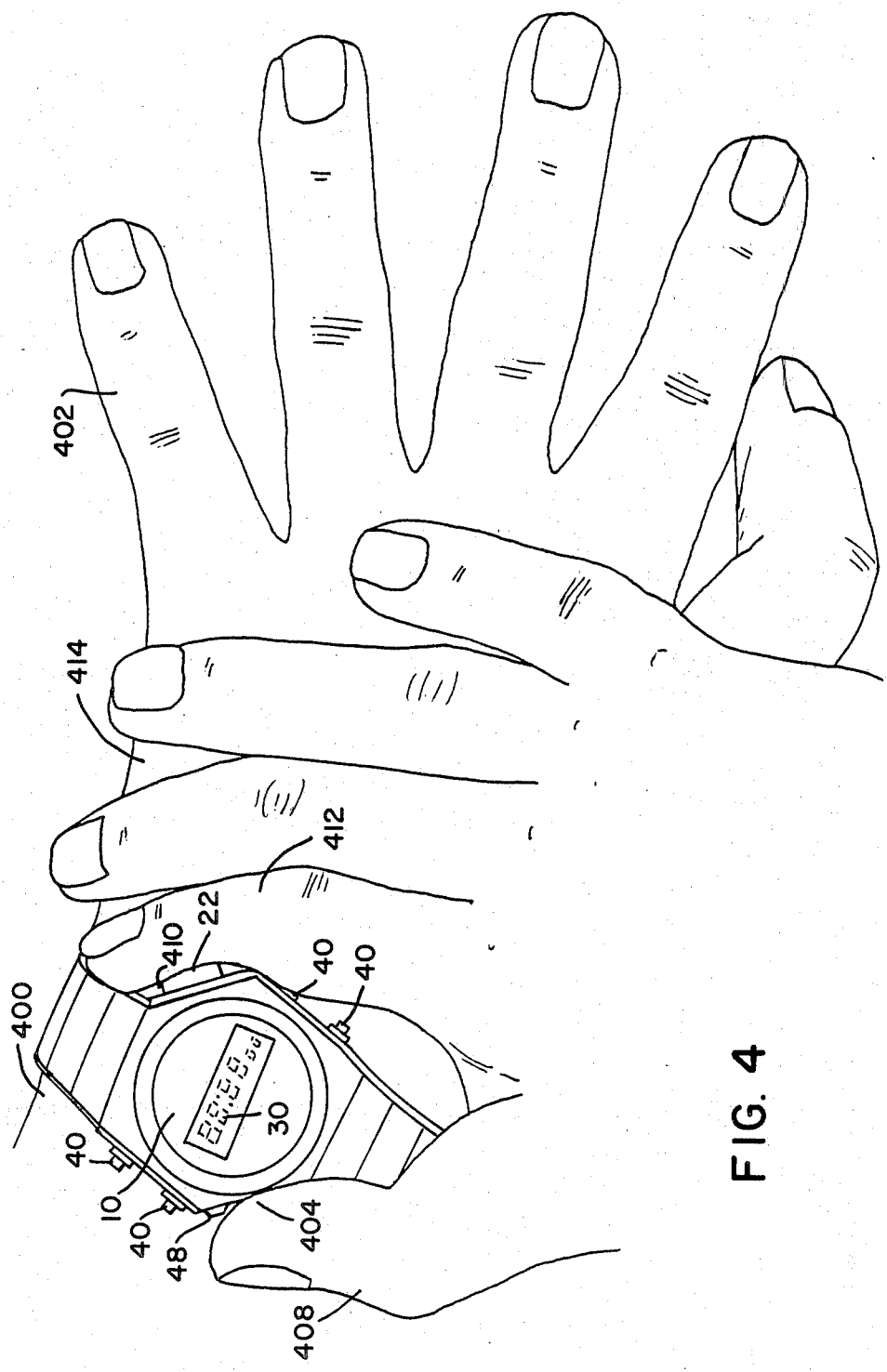
FIG. 4 is a top plan view used to explain the manner in which the device of FIG. 1 is used.

With particular reference to FIG. 4, the wrist device, in use, is commonly worn on the left wrist 400 with the inner surface 26 of the main body 12 contacting the wrist of the wearer thus orienting the display 30 so that it can be conveniently read. In this orientation, sensor 22 is oriented in the upper right-hand quadrant of the device. One of the push-buttons 40 is assigned the task of insuring that the sensor 22 is made active. When this has taken place, the user places a portion of the palmar surface of his right index finger or any other finger over the sensor area 22 while at the same time pressing his thumb against the flap 48, thus capturing the device 10 between the thumb and the index finger. The three remaining fingers of the right hand rest on the back of the left hand. In this arrangement, the device will commence picking up the pulse signal using a photoplethysmographic technique similar to that disclosed in the aforementioned U.S. Pat. No. 4,239,048. Thus, the location of the sensing element 22 enables the user to place his right hand, when the device is worn on the left wrist, on top of his left hand and place his index finger (or any other finger) of the right hand over the sensor 22. It is to be understood that, should the user elect to wear the device on the right-hand wrist, then a portion of the palmar surface of his left index finger will cover the sensor area 22 and the left-hand thumb will cover the flap 48. In this orientation, the palmar surface of the fleshy part of the left-hand palm rests on the dorsal or back surface of the right hand. With continued reference to FIG. 4, in a preferred manner of using the device to measure pulse using the sensor 22, the wrist device is secured about the wrist 400 of the left arm of the user so that the sensor 22, which is located on the side 21 of the body 12 of the wrist device, faces somewhat along the line defined by the fifth metacarpus which is contained in the small last finger 402 of the left hand. In this orientation, the rubber flap 48 lies diagonally opposite the sensor. The user then places the pad 404 of his right-hand thumb 408 against the cover 48. The pad 404 is that portion of the thumb which lies on the palmar surface of the hand near the second row phalange of the first shaft.

At the same time, the user places the pad 410 of the index finger 412 against the sensor 22. The pad of the index finger is that portion of the skin on the palmar surface of the right hand near the third row phalange of the second shaft. The palmar surface of the remaining fingers of the right hand rests on the dorsal surface 414 of the left hand in the area defined by the carpus.

Through this arrangement, an ideal position for sensing pulse is obtained. The movement of the pad of the thumb and the pad of the index finger toward one another with the wrist device interposed therebetween provides a positive, unwavering contact between the pad of the index finger and the sensor 22. Further, by the palmar surfaces of the remaining fingers of the right hand resting on the dorsal surface of the left hand, both hands move in tandem as a unit and thus greatly reduce motion artifact which could otherwise lead to a spurious reading. These advantages also obtain, albeit not as well, when the wrist device is worn on the right wrist and the fleshy part of the left-hand palm rests on the back of the right hand.

Figure 12:
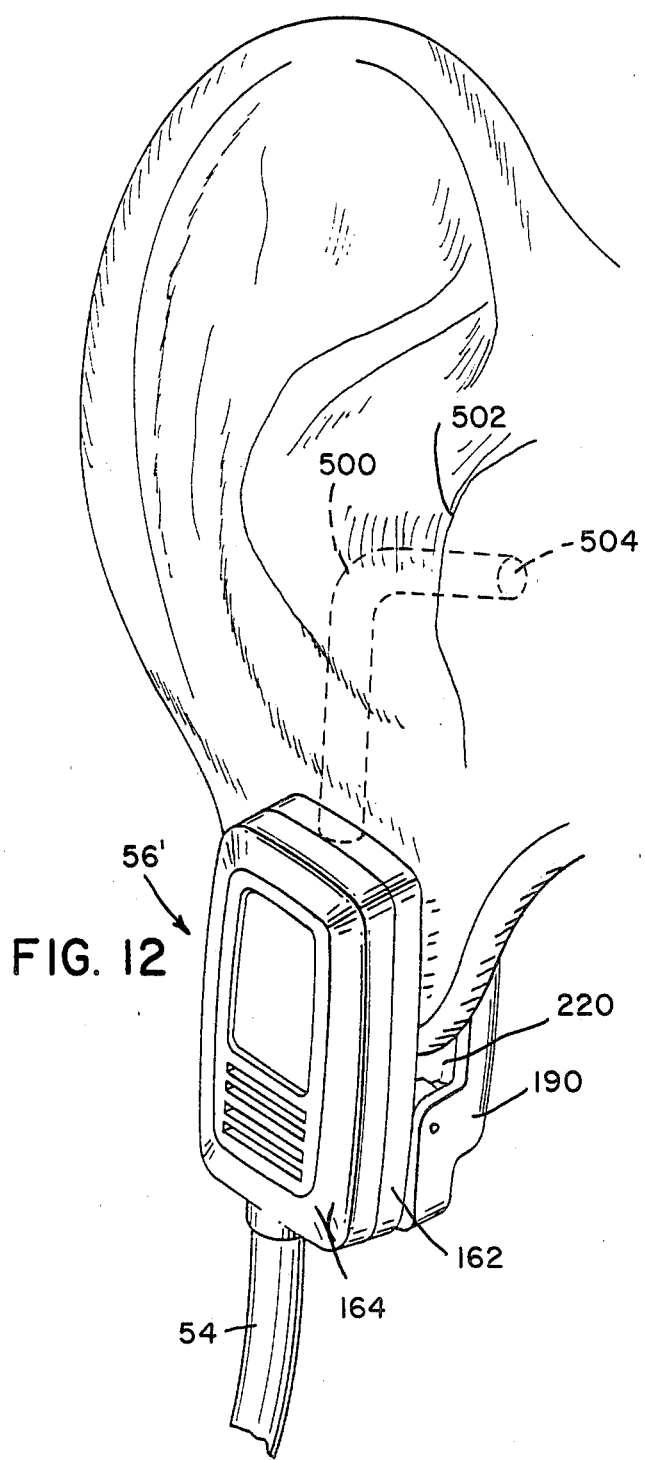
FIG. 12 is a perspective view showing the remote ear sensor in use attached to the earlobe with a remote temperature sensor in phantom.

Should the user desire to measure pulse, or some other physiological parameter, through the use of a remote sensor, the user would remove the resilient plug 48, which is located in the lower left-hand quadrant of the device diagonally opposite from the sensor 22 as described hereinbefore. The removal of the plug allows for the introduction of the connector 52 into the female connector 50 provided in the main body 12 (FIG. 5). On introduction of the connector 52 into the side 44 of the main body, the permanent sensor 22 is disconnected and the remote sensor assembly 56, which is electerically attached to the male connector 52, would be activated so that when it is placed on an appropriate portion of the human body, for example, the finger, it would commence inputting a pulse signal into the circuitry contained within the main body 12. This makes it possible to take a pulse off the finger of the same hand where the device is located or any other finger as well as to take a pulse using a different remote sensor from the earlobe of a user, as shown in FIG. 12.

By providing a sensor on the fingertip, the wrist device enables the user to monitor and read his pulse while he is in motion such as running. The use of the remote ear connector allows for the same function plus it enables the device to receive a clearer signal since the earlobe has no callouses and is full of pulsating blood close to the carotid artery. In addition, the use of a remote ear pulse sensor is especially useful in a medical setting where a nurse may wish to take the pulse of the patient off the ear without the need to search for the pulse as is presently necessary with a fingertip sensor.

One of the important aspects of the present invention is that, through the employment of a remote sensor with connector, the wrist device can be used as a dedicated display of whatever input it receives from the remote sensor. While the illustrated embodiment shows the remote sensor as a pulse sensor, it is well within the knowledge of those skilled in the art to replace that sensor with a remote sensor for monitoring by non-invasive techniques, for example, lung capacity, temperature, respiration, etc.

Because of the advancements being made in the field of microelectronics, it is well within the knowledge of those skilled in the art to provide circuitry within the remote sensor 56 for accomplishing initial processing of the sensed signal and to provide such a process signal to the circuitry within the main body 12 of the wrist device 10. One way in which this can be accomplished is described hereinafter, when considering the details of the circuitry employed in the illustrated embodiment.

Having given a general description of the device along with the manner in which it is intended to be used, the structural details of the device will now be described.

With reference to FIGS. 6–9, the connector assembly 60 includes the female connector 50 defined within the main body 12 of the wrist device 10, and the male connector 52.

Figure 6:
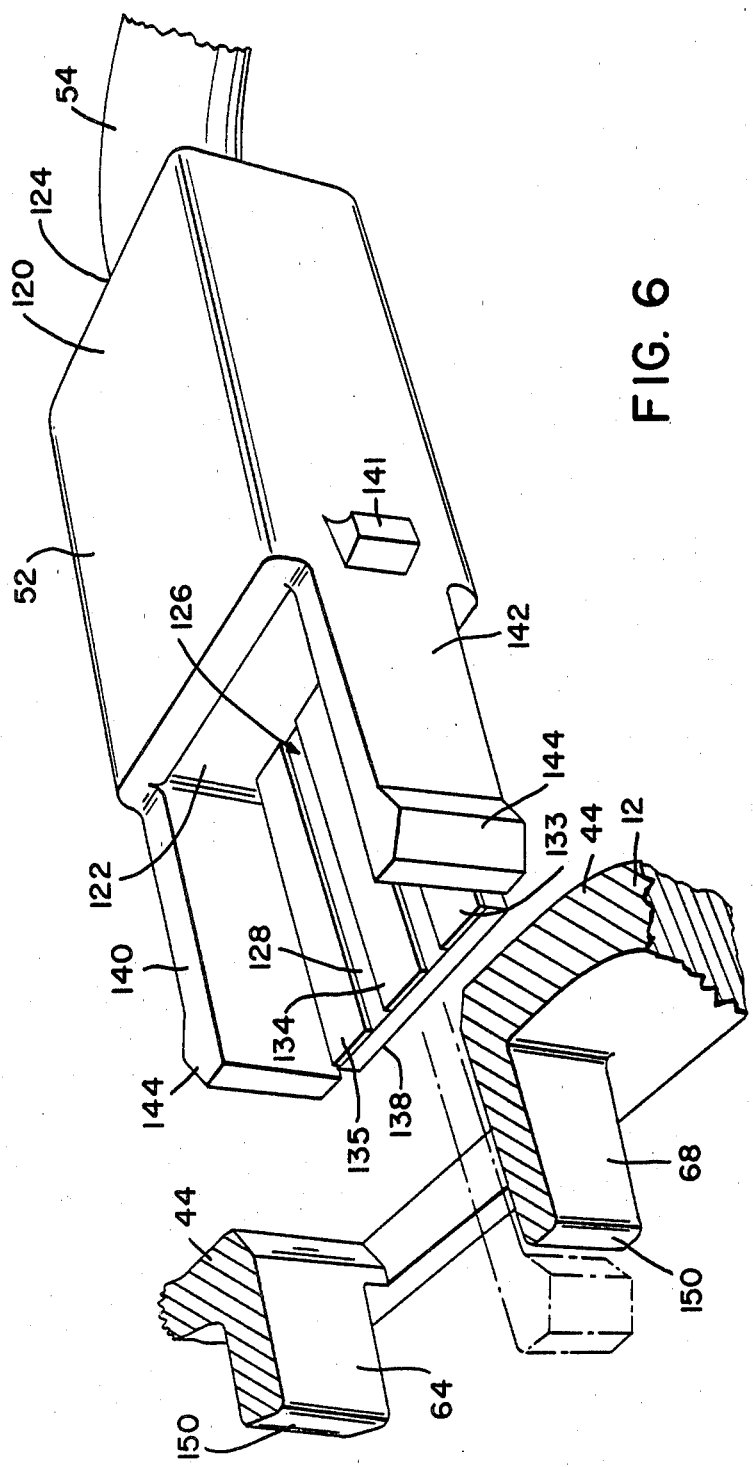
FIG. 6 is a perspective view of the male connector of the connector assembly of FIG. 2 with a portion of the wrist device in section.
Figure 7A:
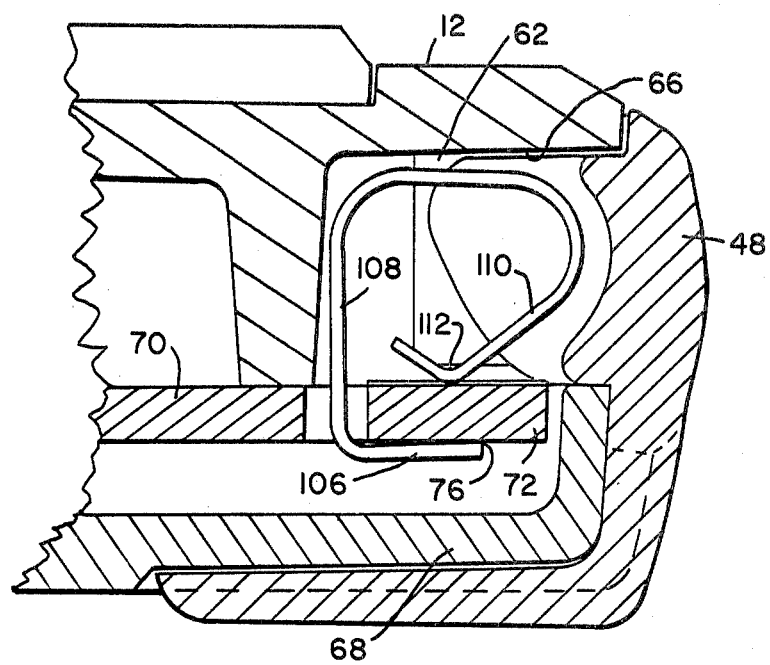
FIG. 7a is a cross-section of the female connector of the connector assembly of FIG. 2 with a cover flap in place.

The interior of the main body 12, as best shown in FIGS. 6 and 7a, defines a cavity 62 within which the female connector is housed. The cavity is defined, in part, by opposed side walls 64 and 68 which emanate from side wall 44 and extend inwardly. The top of cavity 62 is defined by wall 66 which is part of one of the two pieces constituting the main body 12. The bottom of the cavity is generally defined by wall 68 which is part of the other of the two pieces constituting the main body 12.

Figure 7B:
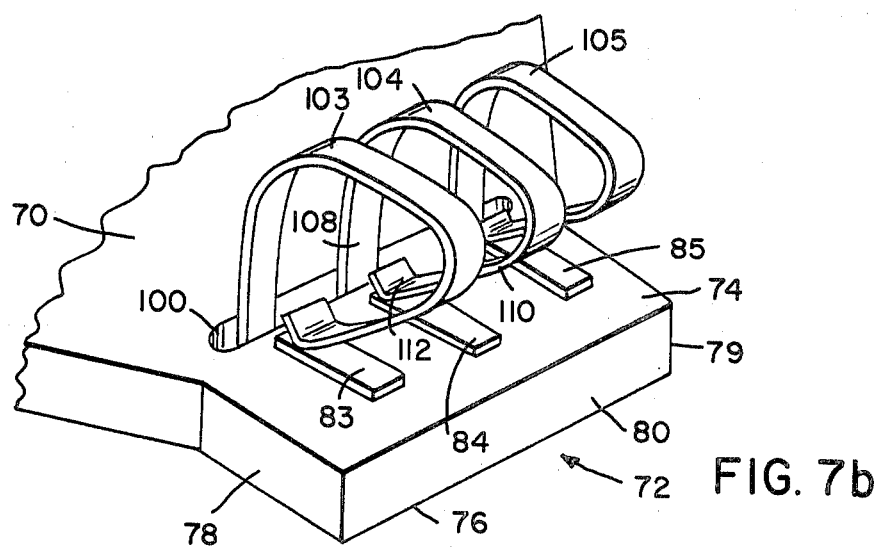
FIG. 7b is a perspective view of the electrical contacts of the female connector.

Mounted within the housing is printed circuit board 70 to which the various elements constituting the circuitry are mounted. The printed circuit board contains an electrically insulated ledge portion 72 which extends into the cavity 62. With reference to FIGS. 7a and 7b, the ledge 72 defines a top surface 74, a bottom surface 76, a pair of opposed side walls 78 and 79, and a front wall 80. The ledge is disposed in the cavity so that side wall 78 is positioned near side wall 68 of the body 12, while side wall 79 is positioned near the side wall 64 of the body. Longitudinally-spaced along the top surface 74 are three electrical contact strips 83 through 85. These strips, through the configuration of the printed circuit boards, are electrically connected to the sensor 22. In a preferred embodiment, the sensor comprises a light-emitting diode 86 in combination with a photocell 88. As schematically shown in FIG. 7c, the diode contains two electrical contact points 90 and 92 while the photocell contains two electrical contact points 94 and 96. Electrical contact point 90 of the diode and 96 of the photocell are electrically connected in common with the conductive strip 84. Conductive point 92 of the diode is electrically connected to conductive strip 85 whereas conductive point 94 of the photocell is connected to electrically conductive strip 83.

The printed circuit board 70 just behind the ledge portion 72 contains a cutout 100. Positioned within the cutout are three spaced spring contacts 103 through 105. Each of the spring contacts is associated with one of the electrically conductive strips 83 through 85. Using spring contact 104 as exemplary, this contact has a lower leg portion 106 mounted to the printed circuit board ledge 72 so as to be electrically connected to the appropriate circuitry contained on the board. From the point of contact of the lower leg 106, the spring then contains a further leg portion 108 which extends upwardly through the cutout 100. The structure of spring 104 then continues and terminates in a loop portion 110, the end of which contains an apex bend 112. Spring 104 is tensioned in such a way that, when it is mounted to the printed circuit board, the apex bend 112 normally makes electrical contact with the strip 84.

Thus, it can be seen that, through the electrically conductive springs 103 through 105 appropriately making contact with the electrical strips 83 through 85, the diode 86 and the photocell 88 are normally electrically operative.

If the user wishes to make use of the remote sensor 56, the male connector 52 must be inserted into the female connector 50, which is contained within the main body 12 of the device. The male connector 52 includes a generally hollow main body portion 120 having a front end 122 and a rear end 124. The wire leads 54, which have one end connected to the sensor 56, have the other end entering the rear portion 124 of the male connector 52. Emanating from the front portion of the male connector 122 is a connecting ledge 126. The ledge, which is made from electrically insulated material, contains a top surface 128 on which is mounted a series of electrically conductive strips 133 through 135. These strips are disposed on the ledge 126 of the male connector 52 in much the same manner as the electrically conductive strips 83 through 85 are disposed on the ledge 72 of the printed circuit board.

The ledge 126 is made of an electrically insulating material commonly used in printed circuit boards. As such, the bottom surface 138 of the ledge is nonconductive. Projecting outwardly from the front wall 122 of the connector 52 are a pair of fingers 140 and 142. The fingers emanate from the front wall 122 in such a way that the ledge 126 is interposed therebetween. Each of the fingers terminates at its free end in a flange portion 144. In a preferred embodiment, the fingers 140, 142 are formed as an integral part of the housing 120.

With reference to FIGS. 2, 6 and 8, the male connector 52 may be mounted within the cavity 62 in the following manner. To insert the connector 52, the flange portions 144 of the legs 140 and 142 initially contact the side walls 64 and 68 of the housing. This contact causes the legs 140 and 142 to bend inward toward the ledge 126. Continued advancement of the connector 52 into the cavity 62 causes the apex 112 of each spring finger 103 through 105 to be deflected under the urging of the ledge 126. In this way, the electrical connection between the spring fingers 103 through 105 and the electrical strips 83 through 85 is broken. At some point during the advancement of the connector into the cavity, the flange portions 144 reach the ends 150 of the side walls 64 and 68. At this point, the legs 140 and 142 are freed to resume their normal position. In this way, the flange portions 144 cooperate with the end portions 150 of the side walls 64 and 68 in order to hold the connector 52 within the cavity 62. Holding of the connector 52 is also facilitated by boss members 141, one defined on each side of the connector 52 just behind each leg 140 and 142. At the same time, the springs 103 through 105 now make contact with the conductive strips 133 through 135 in order to electrically activate the sensor 56.

Figure 10:
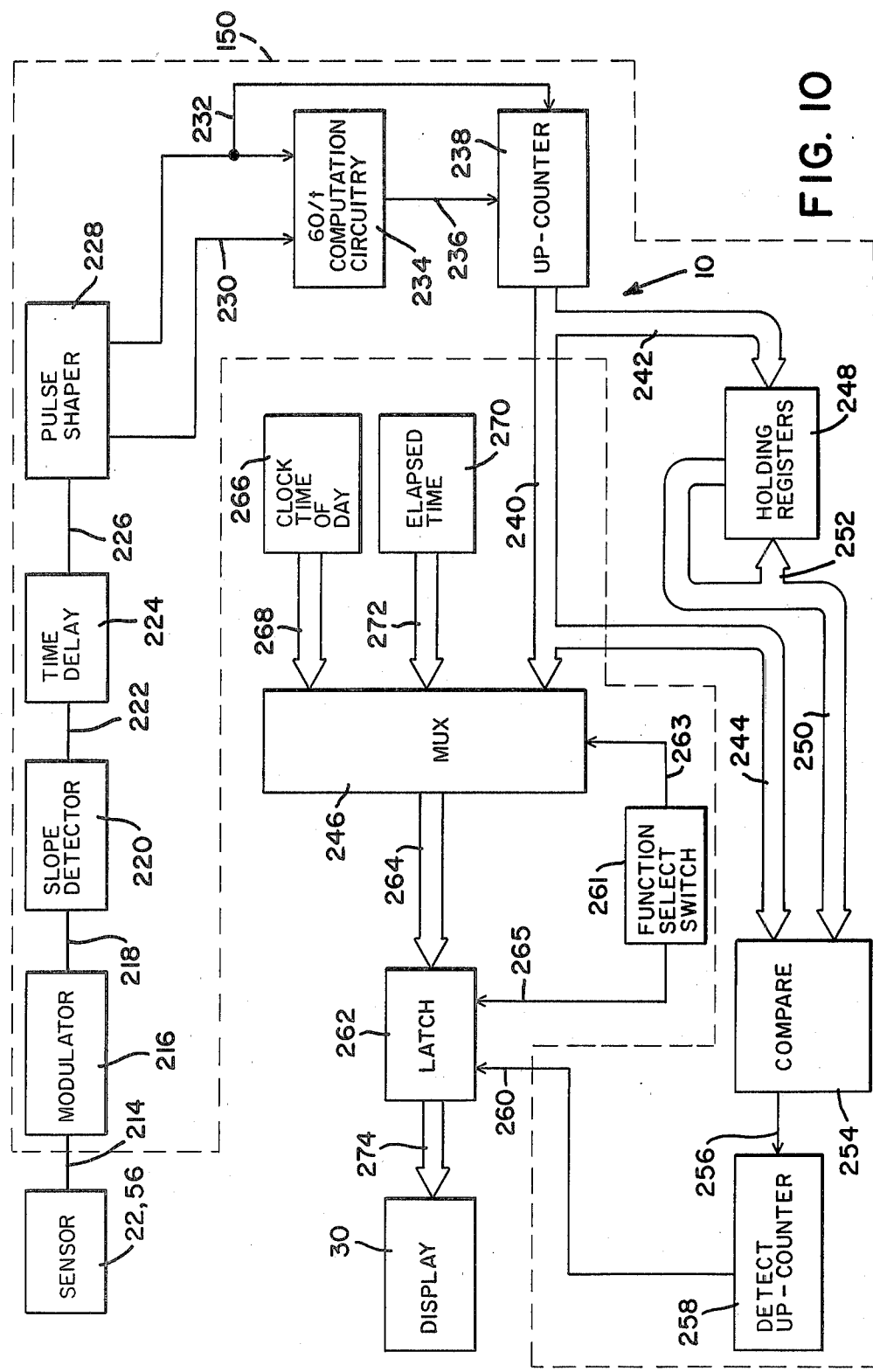
FIG. 10 is a schematic block diagram illustrating the circuitry found in the wrist device and remote sensors.

At this point, it would be appropriate to discuss the details of the circuitry used in both the device 10 and the remote sensor 56. With reference to FIG. 10, a block diagram illustrating such circuitry is shown. The details of the individual blocks are described in much greater detail in copending U.S. patent application Ser. No. 9,823, which has already been incorporated by reference herein. In a preferred embodiment, the sensor, which may be either sensor 22, which is contained in the wrist device, or remote sensor 56, is a light-emitting diode/photocell combination, which measures the systolic beats of the user. The electrical signal produced by the sensor is fed into a modulator 216 via leads 214. The modulator 216 converts the incoming signal into a digital signal for interpretation by a slope detector 220. The output of the slope detector 220 appears on line 222 and is fed to a time delay 224. The output of the time delay appearing on leads 226 is fed to a pulse shaper 228 which produces two pulse trains on lines 230 and 232.

The signals appearing on lines 230 and 232 are fed into a 60/t computation circuitry 234. The signals on lines 230 and 232 cause the 60/t circuit 234 to produce at its output 236, a digital signal having a frequency equal to the number of heart beats per minute.

An up-counter 238 responds to the signal on line 236 by producing an output signal 240 which is a digital representation in binary form of the number of beats per minute. The signal appearing on line 232 is used to reset the up-counter 238 between detected beats.

The output of the up-counter is typically a 12-bit number, D11-D0, which is fed to a multiplexer 246. The multiplexer 246 also receives the output of a time-of-day clock 266 on lines 268, and then elapsed time indicator 270 on lines 72.

At the same time, 6-bits, D7-D2, from the output of the up-counter are fed to holding registers 248 on lines 242 and to a compare 254 via lines 244. The holding registers 248 typically comprise a series of 10-bit shift registers, although a shift register having a capacity for a greater or lesser number of bits can be used. The holding registers are clocked at a rate such that the entire contents of the registers are presented to the compare 254 before the output of the up-counter is changed. The output of the holding registers 248 is also reinserted into the registers on a first-in/first-out basis, along with the output of the up-counter so that the oldest piece of data is replaced by the output of the up-counter.

The compare 254 contrasts the data from the up-counter 240, appearing on lines 244, with the data samples contained in the holding registers 248, appearing on lines 250. When the bits on line 244 are the same as the bits on lines 250, the compare 254 issues a compare signal on line 256.

The detect up-counter, which is typically a conventional up-counter, is caused to advance or count one unit by the compare signal 256. When the detect up-counter has advanced at least two, but typically three, units, a latch pulse is issued on line 260.

A function-select switch 261, which in the preferred embodiment is the push-buttons 40, provides a means for selecting between three functions for display, namely, time-of-day, elapsed time, or heart rate. When heart rate is selected, the multiplexer 246 feeds the output of the up-counter 238 to the latch 262. The signal appearing on line 260 from the detect up-counter 258 causes the latch 262 to issue appropriate signals on lines 274 to cause the display 30 to display, in eye-readable form, the heart rate of the user in beats per minute.

When the user wishes to display the time-of-day or the elapsed time, the function-select switch 61 also activates the latch 262 to produce the appropriate display in eye-readable format on the display 30.

In a preferred embodiment, the circuitry shown in FIG. 10 is implemented on an integrated circuit chip which is mounted on the printed circuit board 70 contained within the wrist device 10. In this case, if it is the intention of the user to only measure pulse, then the remote sensor 56 would only contain the diode 86' and the photocell 88' with no additional circuitry. However, if the user intends to employ the wrist device also as a dedicated display for the measurement of other physiological parameters, then each remote sensor would contain appropriate circuitry for converting the sensed physiological parameter into an appropriate data signal for interpretation and display by the wrist device. By way of example, if the remote sensor is to detect pulse, then the circuitry of FIG. 10 enclosed in dotted lines 151, would be contained within the housing of the remote sensor 56. This circuitry would be implemented through microelectronic techniques so that it could be easily mounted within the housing of the remote sensor. In such a case, power for this circuitry would come from the wrist device 12 and thus the male connector 50 and the female connector 52 would be modified to contain a greater number of spring contacts and electrical strips in order to accommodate additional electrical leads to and from the remote sensor.

Where the remote sensor contains the necessary circuitry for producing the proper information signal, the circuitry within the device 10 comprises the multiplexer 246, the latch 262, the function-select switch 261, and the display 30. The information from the remote sensor is fed into the multiplexer 246 and then, through activation of the proper push-button 40, causes the function-select switch 261 to activate the multiplexer 246 and the latch 262 to transfer the data to the display 30.

Figure 11A:
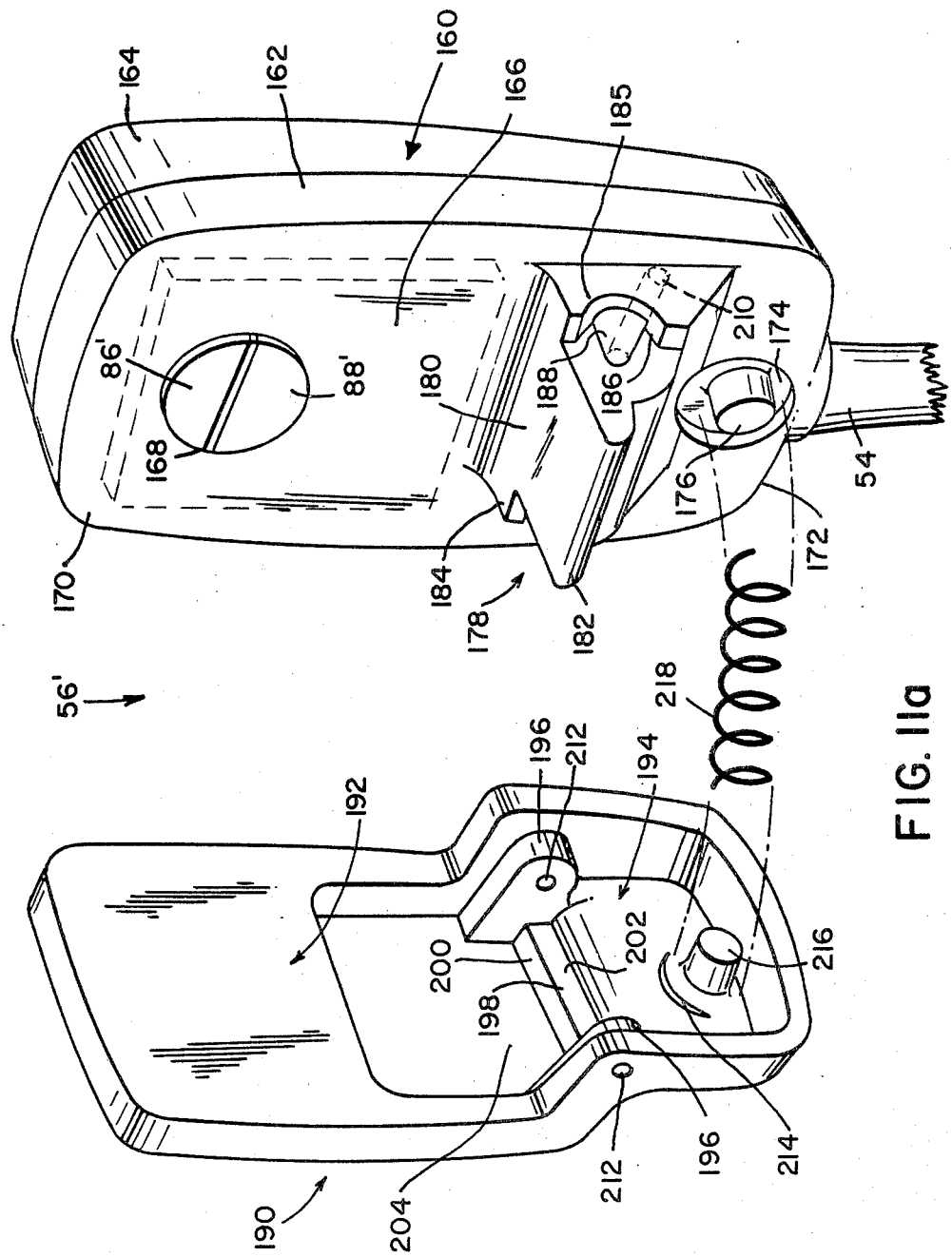
FIG. 11a is an exploded perspective viewed from the right showing an embodiment for a remote ear sensor.
Figure 11B:
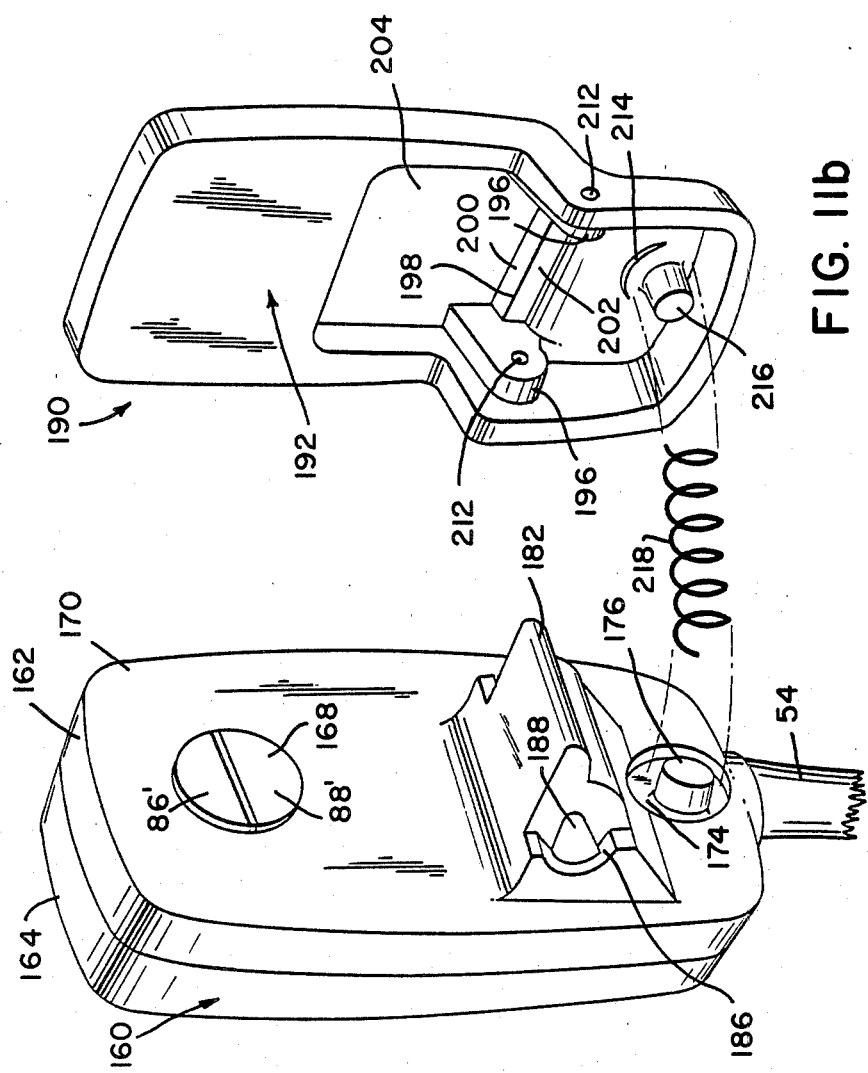
Figure 13:
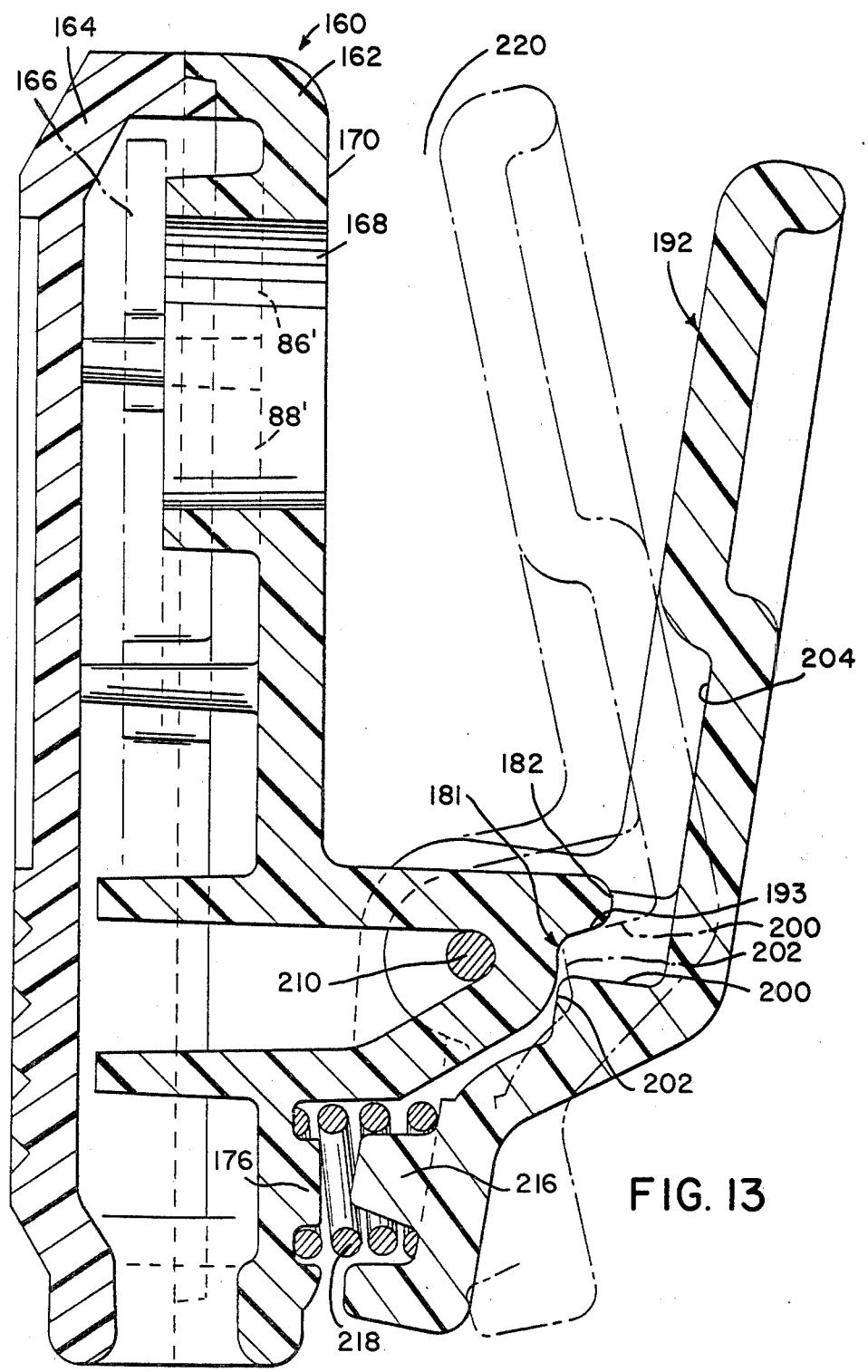
FIG. 13 is a longitudinal section of the remote ear sensor of FIG. 12.

Two examples of remote sensors, one for use on the ear, and one for use on the finger, will now be described in detail. With reference to FIGS. 11 through 13, the remote ear sensor 56' includes an elongated main body portion 160 made up of two parts: a housing 162 and a back cover 164. The body 160, which may be made from plastic, defines a chamber therein for receiving a printed circuit board 166 (shown in phantom). Mounted on the printed circuit board is the diode 86' and the photocell 88', which together constitute the remote sensor. An aperture 168 is provided in a front wall 170 of the housing 162 in order to allow the sensor to protrude. If the remote sensor is to form part of a family of sensors, where the wrist device would be used as a dedicated, universal display, then the printed circuit board 166 would have mounted to it an integrated circuit chip containing the appropriate circuitry for transforming the signal from the sensor into a standardized information signal for interpretation and display by the wrist device.

With reference to the orientation of the ear sensor in FIG. 11, the wire leads 54 from the male connector 52 enter near the bottom side portion 172 of the ear sensor. Defined near the bottom of the face 170 is a spring receiving indentation 174 with a concentric outwardly extending post 176. Extending transversely across the face 170 and positioned slightly above the spring receiving indentation 174 is a pivot structure 178.

The pivot structure 178 includes a central portion 180 which extends outwardly from the surface 170 and terminates in a curved surface 182 that extends transversely across and spaced from the surface 170. Spaced inwardly from the curved surface is a step 181, which is defined by a first generally rectangular flat surface 191 that is substantially parallel to surface 170, and a second substantially flat surface 193 that merges with curved surface 182 and is almost perpendicular to surface 191. The assembly 178 also contains two side portions 184 and 185 which are positioned on either side of the central portion 180. Each of the side portions contains a concave depression 186. Defined within the central portion 180 is an opening 188 which extends across the interior of the main portion 180 in line with the side portions 184 and 185.

A generally elongated paddle 190 completes the structure of the ear sensor 56'. The paddle contains an inner side 192 in which is defined a mounting structure 194 that is configured to mate with the mounting assembly 178. The mounting structure 194 includes a pair of spaced cylindrical portions 196 which are pivotally received in the depressions 186 of the mounting assembly 178. Interposed between the cylindrical portions 196 is a transverse ledge 198. As oriented in FIG. 11, this ledge defines a top surface 200 and a side surface 202. The top surface 200 is substantially normal to an interior surface 204 from which the cylindrical portions 196 emanate in a substantially perpendicular direction. When the paddle is mounted on the mounting assembly 178, the surface 204 pivots about the curved surface 182. The paddle is held in place of the housing of the ear sensor through a pivot pin 210 which extends through apertures 212 defined in the cylindrical portions 196 as well as through the open area 188 of the assembly 178.

As shown in FIG. 11, the bottom portion of the paddle on surface 192 defines a second spring receiving indentation 214 having a concentric post 216. A compression spring 218 is placed in each of the spring receiving indentations 214 and 174 so as to constantly urge surface 192 at the opposite end of the paddle in the direction of the surface 170 of the sensor housing.

To mount the ear sensor on the earlobe, the user grasps the ear sensor so that the thumb and finger of the user cause the bottom portion of the paddle to pivot about the curve surface 182 thus causing the top of the paddle to create an opening 220 within which the earlobe may be received. The ear sensor is then placed on the earlobe so that the sensor is on the inner portion of the ear, although the sensor will also operate when positioned on the outer surface of the earlobe. By ungrasping the ear sensor, the compression spring is then freed to cause the top portion of the paddle to move toward the sensor and thus capture the earlobe between the sensor and the paddle. The tension of the spring is chosen so that the grasping tension of the ear sensor does not stop blood flow when the ear sensor is mounted on the earlobe. With the male connector 52 inserted into the wrist device, pulses may now be sensed by the ear sensor and received by the wrist device for processing and display.

With reference to FIG. 13, the normal closed position of the ear sensor is shown in phantom. In this position, surface 193 of the housing acts as a stop to limit the closure of the paddle. This is accomplished when surface 200 of the paddle engages surface 193 of the housing. This is to ensure that the opening 220 is always of a minimum size so as not to stop blood flow when the sensor is mounted on the ear.

Figure 15:
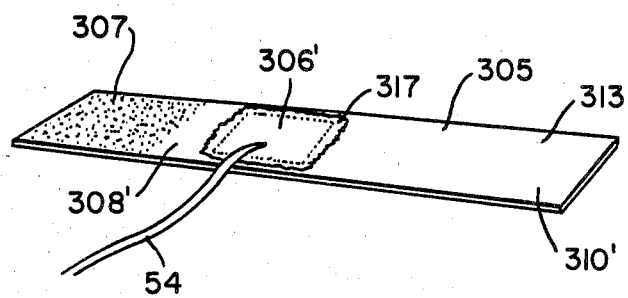
FIG. 15 is a top perspective view of the remote finger sensor of FIG. 14.
Figure 14:
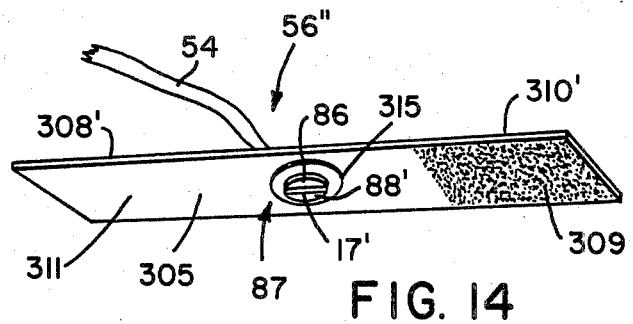
FIG. 14 is a bottom perspective view of an embodiment of a remote finger sensor similar to the one shown in use in FIG. 5.
Figure 3:
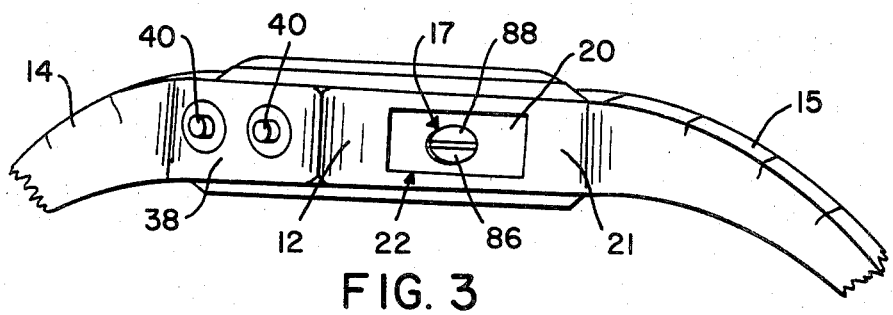
FIG. 3 is a side plan view of the device of FIG. 1 showing an integral physiological parameter sensor.

With reference to FIGS. 5, 14 and 15, an embodiment of a remote finger sensor 56″ will be described. This embodiment includes a single flexible strap 305 which defines an inner or bottom surface 311 and an outer or top surface 313. The strap is nonconductive and may be made, for example, from plastic or cloth. Secured to the central portion of the inner surface by a suitable fastener 315, such as a silicon rubber glue (Silastic) is the diode/photocell sensor 87. The sensor 87 is positioned so that its active surface 17′ is substantially parallel with, and spaced from, the plane defined by the bottom surface of the strap. Affixed to the top surface opposite the sensor is a printed circuit board 306′, which is encapsulated in a Silastic covering 317. It is to be understood that other flexible, nonconductive materials may replace the Silastic. The sensor is electrically connected to the circuitry contained on the printed circuit board 306′. Leads 54 are also electrically connected to the printed circuit board. The printed circuit board 306′ may be dispensed with, in the case where the circuitry for converting the information picked up by the sensor 87 is already present in the wrist device 10.

A series of Velcro loops 307 are longitudinally disposed on the top surface 313 near one end 308′ of the strap 305, while a series of Velcro hooks 309 are longitudinally disposed along the bottom surface 311 near the other end 310′ of the strap 305.

The arrangement of the sensor at the center of the flexible strap results in a conformal electrode of varying size which is readily adaptable to fingers of different diameters. The conformal nature of the electrode ensures optimal contact between the sensor and the portion of the finger where pulse is being sensed.

By securing the sensor 87 to the strap by Silastic ring 315, a conformal electrode of low mass is provided. It has been observed that, by providing low mass, movement artifact is further reduced. In addition, the Silastic allows the sensor to better conform to the pad of the finger without cutting off blood flow. Such would not be the case if a rigid material were used to secure the sensor to the strap. Finally, by spacing the sensor surface 17′ away from the plane defined by the bottom surface 305 of the strap, the sensor is completely embedded in the pad of the finger, thus eliminating ambient light and further reducing the chances of spurious readings.

FIG. 5, illustrates the use of the finger sensor. With the wrist device 10 being worn on the wrist of the left hand 314 of the user, the male connector 52 is positioned within the wrist device and the finger sensor is positioned so that the fleshy tip 316 of one of the fingers covers the sensor surface 17′. The strap ends 308′ and 310′ are then wrapped around the finger with the Velcro loops and hooks making contact across the nail 318 of the finger. It is to be understood that any finger, of any hand, may receive the finger sensor. It only being important that the fleshy part or pad of the finger cover and surround the sensor. This is because the fleshy part contains tiny blood vessels which expand with each pulse.

Since the present system is concerned with the measurement of physiological parameters using noninvasive techniques, remote sensors different from the pulse sensors just discussed could be employed.

For example, lung capacity could be measured through a remote sensor containing a piezo-resistive element or a thermistor. The sensor could then be placed either in the mouth or in the nose and the duration of expulsion of air could be measured and displayed by the wrist device.

A remote sensor for measuring temperature through the employment of a thermistor could also be provided. The temperature could be measured either in the mouth, under the arm, or in the ear canal. In the case of measurement in the ear canal, remote sensor 56′ could contain the temperature sensor structure 500 (shown in phantom in FIG. 12), so that when the ear sensor assembly is mounted on the ear the temperature sensor thermistor 504 could be placed within the ear canal 502 while the pulse sensor is placed on the earlobe. In each of the cases just mentioned, the remote sensor contains the appropriate circuitry, as implemented through employment of microelectronics, to take the sensed parameter and convert it into an information signal which is relayed along leads 54 through the interconnection of connectors 50 and 52 into the wrist device for subsequent processing and display.

From the above, it will be appreciated by those skilled in the art that remote sensors having one or more known physiological parameter measuring devices can be made. The present invention contemplates such a structure as set forth in the specific example concerning the measurement of pulse and temperature at the ear.

Obviously, many modifications and variations of the present invention are possible in light of the above teachings, and it is contemplated that the subject invention may be implemented through the use of discrete components or integrated circuit chips. It is, therefore, to be understood that within the scope of the appended claims, the invention may be practiced otherwise than as specifically described.

What is claimed is:

1. A physiological parameter measuring system for non-invasive measurement of parameters of the body of a user, said system comprising:
a main housing adapted to be carried on the body of the user;
first connecting means mounted on said housing;
a visual display means mounted in said housing;
signal processing and display circuitry electrically connected to said connecting means and said display means, said signal processing and display circuitry for converting a standarized information signal into an eye-readable format on said visual display means, said standardized information signal representing a physiological parameter value to be converted into an eye-readable format by said signal processing and display circuitry without further transformation;

at least two remote sensors, said sensors being associated with at least two different physiological parameters and adapted to be associated with a different part of the body;

each sensor comprising:

a sensor housing;

sensing means mounted on the housing for detecting at least one desired physiological parameter;

second connecting means;

dedicated circuitry within said sensor housing for transforming said detected physiological parameter into said standardized information signal;

means for conveying said standarized information signal to said second connecting means, said second connecting means adapted to conductively mate with said first connecting means in order to transfer said information signal to said signal processing and display circuitry.

2. The system of claim 1, wherein one of said at least two remote sensors is for measuring one physiological parameter and said sensor housing includes means for mounting said sensor on the lobe of an ear of the user.

3. The system of claim 2, wherein the sensor housing of another the other of said at least two remote sensors is for measuring a different physiological parameter and comprises means for mounting said sensor on the fingertip of a user.

4. The system of claim 1, wherein said means for mounting comprises a pair of straps, each of said straps containing a synthetic material such that when the straps are wrapped around the finger, the synthetic materials adhere to each other.

5. The system of claim 2, wherein said sensing means of said sensor mounted on the earlobe of a user comprises first detecting means adapted for contact with the earlobe for detecting a first physiological parameter and second detecting means adapted to be positioned within the ear canal of said ear for detecting a second physiological parameter.

6. The system of claim 5, wherein said first physiological parameter is pulse rate and said second physiological parameter is temperature.

7. The system of claim 1, further comprising permanent sensing means mounted in said main housing for detecting a desired physiological parameter, and wiring means for electrically connecting said permanent sensing means to said first connecting means.

8. The system of claim 7, wherein said first connecting means comprises a cavity within which are positioned a first plurality of electrical contacts conductively connected to said wiring means, and a second plurality of electrical contacts conductively connected to said signal processing and display circuitry, each of said second plurality of electrical contacts being yieldably biased into conductive contact with a particular one of said first plurality of electrical contacts; and said second connecting means comprises a connector having a base portion, a third plurality of electrical contacts disposed on said base portion, means for orienting said connector in a predetermined manner when said connector is inserted into said cavity of said first connecting means, said third plurality of electrical contacts being arranged in a pattern on said base portion, said pattern being the same as the pattern associated with the arrangement of said first plurality of contacts in said cavity, each of said third electrical contacts functionally corresponding to a particular one of said first electrical contacts, the insertion of said male connector into said cavity causing said second electrical contacts to yield and be biased into contact with said third plurality of electrical contacts.

* * * * *